United States Patent
Sanghavi et al.

(10) Patent No.: US 12,151,031 B2
(45) Date of Patent: Nov. 26, 2024

(54) TOPICAL COPPER TRIPEPTIDE COMPOSITION

(71) Applicant: Akshay Sanghavi, Mumbai (IN)

(72) Inventors: Akshay Sanghavi, Mumbai (IN); Kavita Singh, Mumbai (IN); Agnivesh Shrivastava, Mumbai (IN)

(73) Assignee: YUVAN RESEARCH, INC., San Francisco, CA (US)

( * ) Notice: Subject to any disclaimer, the term of this patent is extended or adjusted under 35 U.S.C. 154(b) by 1038 days.

(21) Appl. No.: 16/976,304

(22) PCT Filed: Feb. 27, 2019

(86) PCT No.: PCT/IN2019/050161
§ 371 (c)(1),
(2) Date: Aug. 27, 2020

(87) PCT Pub. No.: WO2019/167070
PCT Pub. Date: Sep. 6, 2019

(65) Prior Publication Data
US 2023/0088926 A1   Mar. 23, 2023

(30) Foreign Application Priority Data
Feb. 27, 2018 (IN) .............................. 201821007475

(51) Int. Cl.
| | |
|---|---|
| *A61K 9/70* | (2006.01) |
| *A61K 8/34* | (2006.01) |
| *A61K 8/73* | (2006.01) |
| *A61K 9/00* | (2006.01) |
| *A61K 33/34* | (2006.01) |
| *A61K 38/06* | (2006.01) |
| *A61K 47/14* | (2017.01) |
| *A61K 47/32* | (2006.01) |

(52) U.S. Cl.
CPC ............ *A61K 9/7084* (2013.01); *A61K 8/345* (2013.01); *A61K 8/731* (2013.01); *A61K 9/0014* (2013.01); *A61K 33/34* (2013.01); *A61K 38/06* (2013.01); *A61K 47/14* (2013.01); *A61K 47/32* (2013.01)

(58) Field of Classification Search
None
See application file for complete search history.

(56) References Cited

U.S. PATENT DOCUMENTS

| | | |
|---|---|---|
| 4,626,539 A | 12/1986 | Aungst et al. |
| 4,797,284 A | 1/1989 | Loper et al. |
| 4,880,633 A | 11/1989 | Loper et al. |
| 9,549,960 B1 * | 1/2017 | Orofino ............... A61K 31/355 |
| 2005/0197282 A1 * | 9/2005 | Patt ....................... A61K 47/02 |
| | | 514/1.1 |
| 2015/0157728 A1 | 6/2015 | Modi |
| 2015/0265530 A1 * | 9/2015 | Xu ......................... A61K 38/06 |
| | | 604/289 |

OTHER PUBLICATIONS

Hostynek et al., "Human skin penetration of a copper tripeptide in vitro as a function of skin layer", Inflamm Res. Jan. 2011; 60 (1) : 79-86. Abstract.

* cited by examiner

*Primary Examiner* — Robert A Wax
*Assistant Examiner* — Quanglong N Truong
(74) *Attorney, Agent, or Firm* — Jacob M. Ward; Ward Law Office LLC

(57) ABSTRACT

The present invention provides compositions of GHK-Cu/copper tripeptide to avoid first pass metabolism including transdermal patch compositions. The GHK-Cu/copper tripeptide is preferably in the form of a gel reservoir having polymer and one or more penetration enhancers. The transdermal compositions release GHK-Cu/copper tripeptide in various release patterns to allow 1-7 times delivery of GHK-Cu/copper tripeptide in a week. The transdermal compositions instantly achieve steady state in rats and the concentration is sustained over at least 12 hrs, preferably over 24 hrs.

16 Claims, 10 Drawing Sheets

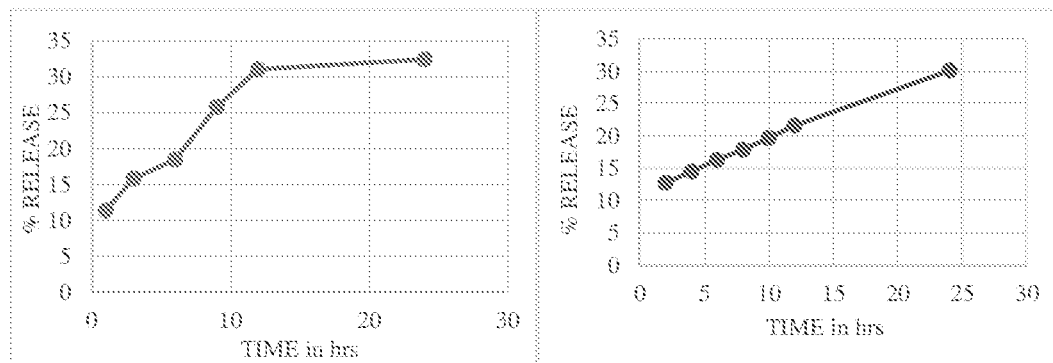
Figure 7A
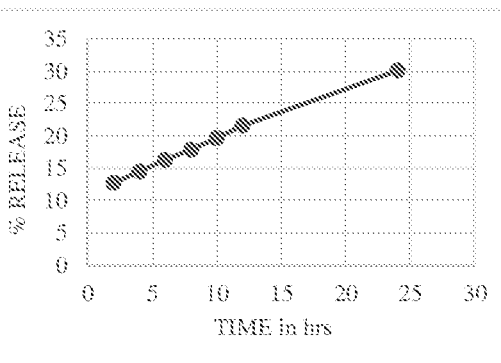
Figure 7B
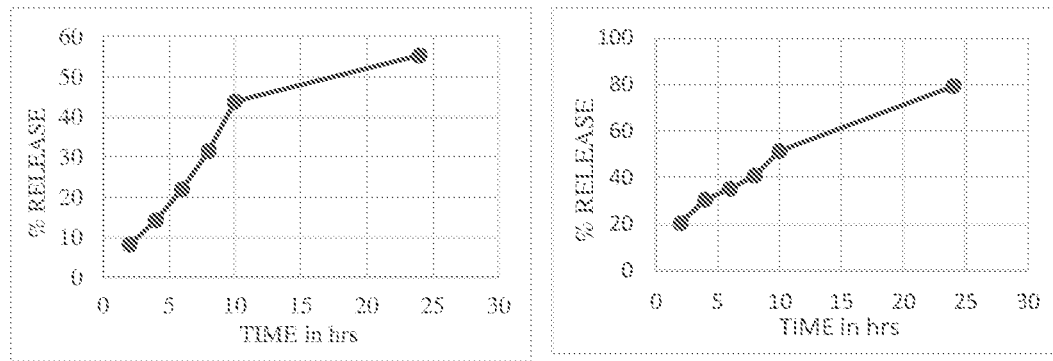
Figure 7C
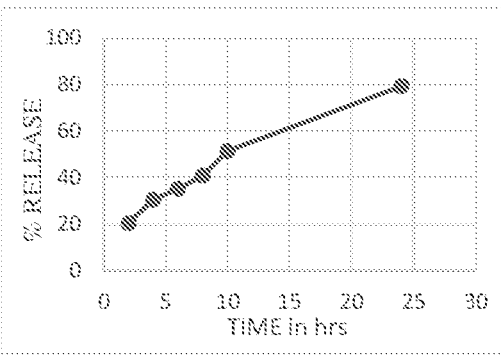
Figure 7D
Figure 7

TOPICAL COPPER TRIPEPTIDE COMPOSITION

CROSS-REFERENCE TO RELATED APPLICATIONS

This patent application is a United States National Stage of International Patent Application PCT/IN2019/050161, filed on Feb. 27, 2019, which in turn claims the benefit of Indian Patent Application No. 201821007475, filed on Feb. 27, 2018. The entire disclosures of the above patent applications are hereby incorporated herein by reference.

FIELD OF THE INVENTION

The invention belongs to the field of pharmaceutical, cosmeceutical and biologics industries. The invention covers delivery systems of a tripeptide, particularly, a glycyl-histidyl-lysin tripeptide in the form of its Cu Complex, hereinafter referred as GHK-Cu or copper peptide. The delivery system includes those which by-pass gut and liver and thus first pass effect/metabolism.

BACKGROUND OF THE INVENTION

GHK (glycyl-L-histidyl-L-lysine) is a human plasma copper-binding peptide with a stunning array of actions that appear to counter aging-associated diseases and conditions. The human tripeptide GHK has a long history of safe use in wound healing and skin care; it is naturally occurring, nontoxic, and is active at a very low nanomolar concentration. GHK was isolated in 1973 as an activity bound to human albumin that caused aged human liver tissue to synthesize proteins like younger tissue. It has a strong affinity for copper and readily forms the complex GHK-Cu. It was first proposed that GHK-Cu functions by modulating copper intake into cells. Since then, it has been established that the GHK peptide has stimulating and growth-promoting effects on many cells and tissues such as chondrocytes, liver cells and human fibroblasts. Subsequently, researchers found that GHK-Cu can stimulate the synthesis of extracellular matrix macromolecules, such as collagen and glycosaminoglycan. It can activate the production of metalloproteinases and anti-proteases that remove damaged proteins from the extracellular matrix macromolecules. GHK-Cu was also found to increase decrorin expression and decrease TGF-beta expression, which is beneficial for a scar-free healing. The increased expression of p63 of keratinocytes by both GHK-Cu and GHK suggests that GHK and its copper complex can promote the survival of basal stem cells in skin. These contribute to increase in sternness and stimulates integrin secretion in human epidermal basal keratinocytes, as well as has a strong wound-healing and tissue-repairing effect.

Developing suitable delivery systems of GHK-Cu is quite challenging. It has a very short elimination half-life of 1.5-2 hrs. This means out of 100% GHK-Cu absorbed, 50% is eliminated in less than 2 hrs. This means achieving a steady state is difficult wherein GHK-Cu should be in sufficiently uniform amounts in plasma to produce action. The GHK-Cu is not stable at gastrointestinal conditions. Some research data reports that owing to short half-life, GHK should be injected two to three times a day. This is very painful and arduous administration. It is also reported that owing to short half-life of the copper peptide, it is recommended to use it when you need it"

OBJECT OF THE INVENTION

The first object of the invention is to provide a delivery system for a tripeptide GHK-Cu to avoid a first pass effect/metabolism. Such delivery systems include transdermal, nasal, buccal, sublingual and injectable dosage forms.

The second object of the invention is to provide a delivery system for a sustained or a controlled delivery of a tripeptide GHK-Cu. This avoids multiple dosing and provides greater patient compliance.

The third object of the invention is to provide a delivery system effecting delivery of therapeutically effective amounts of a potent drug GHK-Cu at a steady-state delivery rate.

The fourth object is to select suitable ingredients for transdermal delivery of GHK-Cu to achieve sustained or controlled action.

SUMMARY OF THE INVENTION

The first aspect of the invention is to provide a delivery system for a tripeptide GHK-Cu to avoid a first pass effect/metabolism. The four primary systems that affect the first pass effect of a drug are the enzymes of the gastrointestinal lumen, gut wall enzymes, bacterial enzymes, and hepatic enzymes. A delivery system free of first pass effect include transdermal, nasal, buccal or sublingual, suppositories and injectables Under this aspect, a delivery system is such that it delivers GHK-Cu peptide in various release pattern so as to provide continuous supply of GHK-Cu over extended periods.

In a second aspect, the invention provides a sustained release of GHK-Cu peptide. Multiple release patterns to address multiple problems are provided such as a 12 hrs release delivery, a 24 hrs release delivery, a 48 hrs release delivery and a 72 hrs release delivery systems.

A 12 hrs delivery system releases more than 80% and preferably more than 90% in 12 hrs.

A 24 hrs delivery system releases more than 80% and preferably more than 90% in 24 hrs.

A 48 hrs delivery system releases more than 80% and preferably more than 90% in 48 hrs.

A 72 hrs delivery system releases more than 80% and preferably more than 90% in 72 hrs.

A controlled delivery system having non-uniform release of GHK-Cu peptide with more release at the beginning and towards the end and less release in between. Multiple release transdermal delivery systems are designed to achieve slow and steady and gradual release, also optionally with low intermittent release when desired, of GHK-Cu in such a manner that the rate of release of GHK-Cu solves the problem associated with elimination to half of its original content every 2 hrs.

The third aspect of the invention is to provide a delivery system effecting delivery in such a way so as to achieve a steady state concentration of GHK-Cu or copper peptide. Any other form of delivery may cause sudden rise and fall in plasma concentration of GHK-Cu. In human plasma, GHK is present at about 200 micrograms/litre in men of age 20-25 but declines to 80 micrograms/litre by the age 60 to 80 years. A transdermal delivery system designed according to the present invention achieves this objective. For example, the fabricated patch of the transdermal delivery system containing from around 0.5 mg to 200 mg of GHK-Cu per patch intended for a 12 hrs/24 hrs/48 hrs/72 hrs delivery aims to provide GHK-Cu in controlled manner to provide additional 120-140 microgram/litre of GHK-Cu to obtain the drug plasma level up to 200 microgram/litre.

The third aspect provides achieving steady state concentration using a sustained/controlled release dosage form of GHK-Cu. Under this aspect, aim is to provide at least 120-140 mcg/litre of plasma over at least 12 hrs, preferably over at least 24 hrs period, more preferably over at least 48 hrs and most preferably over at least 72 hrs.

The fourth aspect is to select suitable ingredients for transdermal delivery of GHK-Cu to achieve sustained or controlled action.

BRIEF DESCRIPTION OF DRAWING

FIG. 7 provides In-vitro release of a transdermal patch incorporating batch 2 (FIG. 7A); batch 7 (FIG. 7B); batch 10 (FIG. 7C) and batch 11 (FIG. 7D).

DETAILED DESCRIPTION OF THE INVENTION

Figure 1:
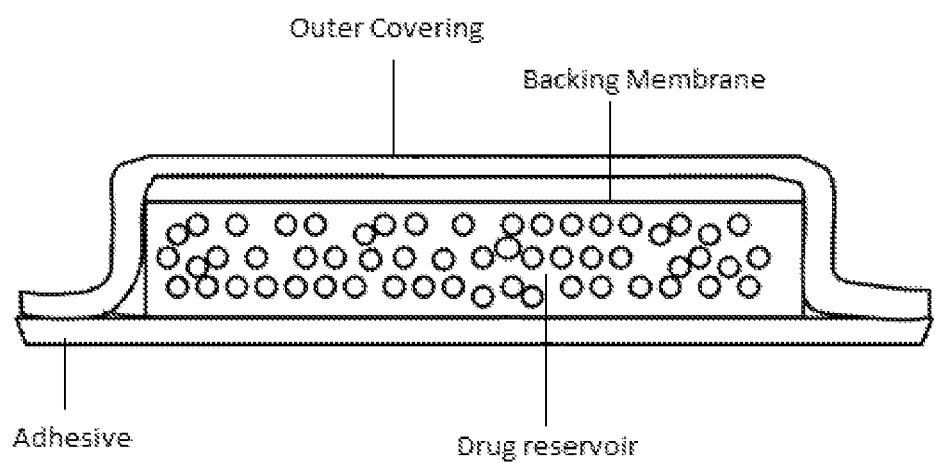
FIG. 1 provides design of a transdermal patch according to the present invention.

The human tripeptide GHK was discovered in 1973 as an activity in human albumin that caused old human liver tissue to synthesize proteins like younger tissue. It has high affinity for copper ions and easily forms a copper complex or GHK-Cu. In addition, GHK possesses a plethora of other regenerative and protective actions including antioxidant, anti-inflammatory, and wound healing properties.

The present invention provides various delivery systems for GHK-Cu so as to achieve multiple goals. Under the first aspect, the delivery system is one which involves avoiding a first pass effect/metabolism. Such delivery systems include transdermal, nasal, buccal, sublingual and injectable dosage forms.

This aspect provides following advantages
  i) Difference between the dose administered and amount absorbed is less
  ii) High dosage is not required
  iii) Safe even in diseases such as liver Cirrhosis
  iv) Drug interactions are less
  v) Variations in Plasma levels are minimum.

One of the preferred delivery systems to avoid first pass effect is a transdermal delivery system. Skin of an average adult body covers a surface of approximately 2 m$^2$ and receives about one-third of the blood circulating through the body. The transdermal route of administration cannot be employed for many drugs. The rationality of drug selection based on pharmacokinetic parameters and physicochemical properties of the drug are the important factors to be considered for deciding its suitability of drug for delivery by transdermal route. Although, skin is one of the most readily accessible organs of the human body, it is very difficult barrier to the ingress of materials allowing only small quantities of a drug to penetrate over a period of time.

Few ideal properties of the drug that can be administered transdermally require that drug should be essentially non-irritating, dose should be preferably up to 20 mg or less and partition coefficient in octanol/water should be between 1 to 4. In case of GHK-Cu peptide, no dose estimation by a transdermal route is done before. The factors which are to be considered for dose estimation by transdermal route are discussed in the literature and are in general as enumerated in table 1

TABLE 1

Factors for consideration for Transdermal Dose Calculation

| Physiochemical | Pharmacokinetic | Biological |
|---|---|---|
| Solubility | Half-life | Skin toxicity |
| Crystallinity | Volume of distribution | Site of application |
| Molecular weight | Total body clearance | Allergic reactions |
| Polarity | Therapeutic plasma concentration | Skin metabolism |
| Melting point | Bioavailable factor | Skin permeability |

Thus, dose calculation requires thorough consideration of all above factors. Accordingly, the present invention provides a transdermal delivery system in the form of a transdermal patch for the GHK-Cu or copper tripeptide. The delivery system preferably is a gel-based system. The transdermal patch may contain from 0.5-200 mg of copper tripeptide, preferably from 1-100, 1-50 and most preferably from 1-20 mg of copper tripeptide.

The amount of copper peptide in a gel is from 0.05-1% of the total gel composition, preferably from 0.1% to 1% of the gel composition. In an embodiment, the copper tripeptide is 0.1%. In another embodiment, the amount of copper peptide is 1%.

Considering very short half life of copper peptide viz. 50% elimination in just 2 hrs, sufficient dose is provided so that levels of copper peptide should not drop over at least 6 hrs, preferably for at least 12 hrs, more preferably for at least 24 hrs and most preferably for at least 48 hrs.

The present invention provides copper peptide reservoir in gel form wherein gelling agent selected makes sustained release of copper peptide over considerable long time such that the patch shall not be changed over 12 hrs, preferably over 24 hrs and most preferably over 48 hrs. Alternatively, it is possible to apply transdermal patches of the present invention 1-7 times a week; preferably 1-5 times a week and most preferably at least 1-3 times a week.

In an embodiment, dose of 1 mg of copper peptide is present in a patch. In another embodiment, a dose of 2 mg-10 mg of copper peptide is present in a patch. In yet another embodiment, the patch contains 20 mg of copper peptide. It is further possible to enhance dose to up to 100 mg or up to 200 mg of copper peptide. Such systems provide further sustained actions and stronger reservoirs. However, patient may want to change the patch over 24 hrs for comfort and he or she may want to wear fresh patch after bath each day. Thus, dose of 1-20 mg, preferably 10-20 mg are found sufficient for a day's application so that wastage is minimized, and the treatment shall remain economical. Additionally, patient/user may want drug free periods/intervals which is also taken care by the invention.

The transdermal system according to the present invention is preferably a gel reservoir for the copper tripeptide. Thus, the drug reservoir may not be able to provide the entire dose In vivo. For example, Rxlist.com reports that in case of nitroglycerin patches only 10% of Nitroglycerin dose is released after 12 hours and the remainder of the nitroglycerin in each system serves as a reservoir and is not delivered in normal use. Further, short half life of GHK-Cu wherein 50% is eliminated in less than 2 hrs makes the situation extremely challenging. Whatever dosage form of GHK one may develop, multiple dosing becomes necessity. There are multiple references wherein copper tripeptide injections are used multiple times over 24 hrs period. The frequency may go as high as 12. To avoid this, under second aspect, the invention provides a sustained release or controlled release transdermal delivery systems. The release can be sustained such that only 30% of copper peptide is released over 24 hrs. However preferably, the release is sustained such that at least 50% of copper peptide is released over 24 hrs. Preferably, around 70-80% of copper peptide is released over 24 hrs. Preferably at least 90% of copper peptide is released over 24 hrs.

Accordingly, inventors of the present invention have provided various embodiments showing at least 30%, at least 50%, at least 70% and at least 90% release over 24 hrs when tested in an In Vitro study using a Franz Diffusion Cell employing a dialysis membrane with 12-14 kd molecular weight cut off.

Further challenge is tolerance to drug. It is expected that such tolerance may not be critical as GHK-Cu exists naturally in human body. However, for a delivery system it should be possible to incorporate drug free interval if needed to avoid tolerance. Thus there is a need to develop a delivery system that will deliver GHK-Cu over long periods and at desired time intervals. This makes it necessary to develop sustained or controlled release transdermal patches under second aspect. Under the second aspect, the sustained and controlled release transdermal patches are developed and tested for In-vitro release. For In vitro study: 2 g of formulation was taken for in vitro diffusion study using Franz diffusion cell in phosphate buffer pH 7.4 at 37° C. across dialysis membrane with 12-14 kd molecular weight cut off, under continuous stirring.

In an embodiment, a transdermal patch of GHK-Cu peptide is developed. The GHK-Cu is released in substantial amounts in 12 hrs. from the patch. The substantial amount is at least 70-80% in 10-12 hrs, preferably at least 90% in 12 hrs and most preferably at least 95% in 12 hrs. One patch can be applied per day and 10-12 hrs of drug free period can be provided. In an embodiment, batch G provides 96% release in an In Vitro Study. Batch G has 1 mg dose of copper peptide (0.05% of 2 g gel). In yet another embodiment, batch H which has 1 mg copper peptide provides 93% release in 12 hrs.

In another embodiment, a transdermal patch is developed that had released at least 50% in 12 hrs and not more than 20% for next 12 hrs. Batch 10 provides at least 50% release in 12 hrs and not more than 20% release in between 12-24 hrs.

In yet another embodiment, not more than 50% is released in 24 hrs. Batches 2 and 7 provide in vitro release of 32.4 and 30.1% respectively in 24 hrs. These batches release substantial amount of copper tripeptide over 72 hrs.

The third aspect provides achieving steady state concentration using a sustained/controlled release dosage form of GHK-Cu. Under this aspect, aim is to provide at least 120-140 mcg/litre of plasma over at least 12 hrs, preferably over at least 24 hrs period, more preferably over at least 48 hrs and most preferably over at least 72 hrs. Inventors of the present invention have conducted In Vivo studies using batch no. 11 on Sprague Dawley rats. The $AUC_{0-24\ hrs}$ is 310.41 µg*h/ml. The invention provides an embodiment which provides a sustained concentration of copper peptide in vivo of 12+2 mcg/ml over 24 hrs from the time of administration.

The fourth aspect provides selection of suitable formulation ingredients to provide a transdermal delivery system providing desired release. Typically, a matrix type and a reservoir type transdermal systems are developed. A reservoir type system is found suitable in the present case because of following reasons.

The suitable ingredients studied to develop a transdermal delivery system releasing GHK-Cu over at least 12 hrs included following ingredients:

A polymer in which the drug is dissolved or dispersed. Polymer could be ionic, non ionic, pH sensitive, heat sensitive or pressure sensitive;

A plasticizer which may be functional;

A solvent and co-solvent which could be any oil, water or organic solvent;

A penetration enhancer which could be solid, semisolid or liquid;

A surfactant which could be ionic, non-ionic in liquid, semisolid or solid form;

A co-surfactant which could be ionic, non-ionic in liquid, semisolid or solid form;

A filler which may be functional.

Development involved developing matrix and drug reservoir type transdermal patches using i) several polymers such as Polyethylene glycol, methacrylate copolymers (Eudragits), Acrylic copolymer, Polyster Film/copolymer of ethylene and vinyl acetate, Poly(Butyl methacrylate, methyl methacrylate), cellulose (Ethyl cellulose, Hydroxypropylmethylcellulose Polyvinylpyrrolidone etc. and ii) permeation Enhancers such as Dimethyl sulfoxide(DMSO), Dimethyl formamide, Ethanol, Propylene glycol, Octyl alcohol, Caprylocaproyl polyoxyl-8 glycerides and diethylene glycol monoethyl ether, Ethyl oleate, Isopropyl myristate, Glyceryl monolaureate, Silicone oil etc. The preferred polymer is polymer of acrylic acid crosslinked with allyl ethers of polyalcohols. The preferred penetration enhancer is one or more of Caprylocaproyl polyoxyl-8 glycerides, diethylene glycol monoethyl ether, Isopropyl myristate. The backing laminate can be of any of the Aluminium vapour coated layer, plastic, film (polyethylene, polyvinyl chloride, polyester) and Heat seal layer.

Release liner can be of Paper fabric, Polyethylene, Polyvinylchloride, Polyester foil and Metalized laminate. Adhesive Layer-Polyacrylate DuroTak 87-4287.

Placebo Trials

In developing a transdermal delivery system, Gel Drug reservoir system is selected. Prior art literature such as U.S. Pat. Nos. 4,797,284 and 4,880,633 had employed propylene glycol as a penetration enhancer which is gelled with 2 percent hydroxypropyl guar (HP-60 Jaguar from Celanese) which served as a dissolved drug reservoir. U.S. Pat. No. 4,626,539 disclosed that the preferable carrier vehicle in a transdermal system comprised 30-80% of propylene glycol. According to these teachings, a transdermal placebo gel preparation are prepared using either of carbomer and HPMC as polymers/gelling agents and 30% of propylene glycol is chosen as penetration enhancer/vehicle. Water is used in amounts of 20%. The data is provided in comparative example 1 and 2. In the compositions of comparative example 1, when HPMC polymer is used, gel formation did not take place but the precipitation was observed as provided in FIG. 2 and the trials failed. Carbomer was used in place of HPMC as polymer/gelling agent and placebo transdermal gels are prepared as provided in comparative example 2. The white gel like product is formed as provided in FIG. 3 which had no transparency. The monophasic white coloured gel did not have desired gel like properties. From above experiments, Carbopol is considered more suitable than HPMC as polymer/gelling agent.

After several trials it was noted that all vehicles/permeation enhancers don't produce quality transdermal gel preparations, particularly at desired pH of 7.4 which is desired pH for Carbopol crosslinking.

Hence, a simple batch comprising carbomer, water and triethanolamine to adjust pH at 7.4 was successfully prepared as a transparent gel and then several vehicles/permeation enhancers were tried.

GHK-Cu Dose Calculation

A preformed GHK-Cu complex can be procured or 1:1 Complex of GHK with copper (GHKCu) is prepared by mixing equimolar solutions of GHK and CuCl2. For this, equimolar GHK and $CuCl_2 \cdot 2H_2O$ are dissolved in distilled water and separately and both the phases are mixed to get complex GHK-Cu.

Considering every 50% of dose is eliminated from the human body in around 2 hrs time, for X mg of dose following pattern as provided in table 2 will be observed. The maximum theoretical dose that can be preferably loaded in a typical transdermal delivery system is 20 mg. However, inventors have found that for GHK-Cu peptide it is possible to include a dose of up to 200 mg in a transdermal patch. Even if theoretical highest dose of 20 mg is provided, at the end of 24 hrs, the amount of GHK-Cu remaining will be 20/4096=0.0048 mg=4.8 mcg.

TABLE 2

Dose OF GHK-Cu remaining in body considering half-life of 2 hrs.

| Time in hrs | Assumed dose administered | Actual drug remaining after 20 mg (X) is administered 0 hr. |
|---|---|---|
| 0 hrs | X mg | If X is 20 mg |
| 2 hrs | X/2 | 10 mg |
| 4 hrs | X/4 | 5 mg |
| 6 hrs | X/8 | 2.5 mg |
| 8 hrs | X/16 | 1.25 mg |
| 10 hrs | X/32 | 0.625 mg |
| 12 hrs | X/64 | 0.3125 mg |
| 16 hrs | X/256 | 0.078125 mg |
| 24 hrs | X/4096 | 0.004882 mg |
| | | Thus, 4.8882 mcg of GHK-Cu complex will remain at the end of 24 hrs after administration of 20 mg of GHK-Cu at 0 hr. |

In human plasma GHK is present at about 200 micrograms/litre in men of age 20-25 but declines to 80 micrograms/litre by age 60-80. Hence, it is necessary to provide at least 120-140 micrograms/litre or 330-385 micrograms per 2.75 litres of plasma. This means even if theoretical highest dose is administered and delivered in body, one can't deliver GHK-Cu in sufficient quantities over period of 24 hrs. The above calculation has considered that the entire 20 mg dose is available to the body. However, entire dose from the drug reservoir rarely will be made available to the body. Around 1-20% of drug from the dose becomes available to the body by a transdermal route. Additionally, in the present case, the copper peptide level drops to 50% of its original levels in every 2 hrs. This was a major challenge. Several experiments were conducted to achieve multiple goals. Suitable gel formation with transparency and spreadability was required. It was required to incorporate dose less than or equal to 20 mg per patch and still deliver at least sufficient amount at the end of 24 hrs considering half-life of around or less than 2 hrs.

It was observed that GHK-Cu did not release well from the gel comprising carbomer, water and triethanolamine which was finalized during placebo trials. The maximum release at the end of 24 hrs remained in the range of 5-35% when tested using dialysis membrane. Later some batches showing around 30% release in 24 hrs are found to exhibit substantial release over 72 hrs.

Further development and experimentation surprisingly led to the present invention wherein with the help of selection of suitable ingredients in appropriate amounts, suitable In-vitro release pattern was obtained wherein even with lower doses, one can deliver sufficient GHK-Cu so that at least 100 micrograms, preferably 200 micrograms and most preferably 300 micrograms of GHK-Cu remain at the end of 24 hrs. This is achieved at the lower dose level and not at the maximum theoretical dose level (20 mg) to incorporate changes required if In-vivo release is much slower than In-vitro release. Thus, inventors of the present invention have now successfully developed transdermal gel compositions that can be applied in the form of a transdermal patch to deliver GHK-Cu in sufficient amounts over at least 12 hrs and preferably over 24 hrs.

Diethylene glycol monoethyl ether, Transcutol P is a known penetration enhancer in topical delivery systems. Further it is safe and has no/low skin irritancy. Transcutol P from 0.5 to 50% is found useful. For 1 mg dose or lower, up to 10% of transcutol p was found useful. For higher doses such as 10-20 mg or higher, up to 50% of transcutol p such as from 20%-40% is found useful. Thus, amount of transcutol p preferably from 0.5-10, more preferably from 1 to 8% and most preferably from 2-6% is found to provide at least 40-80% release in 12 hrs for lower doses. The amount of transcutol p preferably from 10-50%, more preferably from 10 to 40% and most preferably from 20-40% is found to provide at least 40-80% release in 12 hrs for higher doses of copper peptide such as 10 mg or higher or 20 mg and higher.

In an embodiment, adding around 4-4.5% transcutol p provided 40% In-vitro release in 4 hrs and at least 60% In-vitro release in 8 hrs.

Further release enhancement is achieved by choosing second penetration enhancer. Thus, the dual penetration enhancer is found most preferred in the present invention. Several second permeation enhancers along with Transcutol P provided enhanced release pattern as provided under example 2. The second penetration enhancer is preferably polyoxylglyceride. Suitable include Caprylocaproyl polyoxylglycerides, Lauroyl polyoxylglycerides, Linoleoyl polyoxylglycerides, Oleoyl polyoxylglycerides, Stearoyl polyoxylglycerides.

In an embodiment, the second penetration enhancer is Caprylocaproyl polyoxylglyceride. The Caprylocaproyl polyoxylglyceride is used in amounts from 0.5-25%, preferably from 5-25% and most preferably from 10-20% of the composition.

The transcutol P and Caprylocaproyl polyoxylglyceride are used in a ratio of from 20:1 to 1:20, preferably from 10:1 to 1:10 and most preferably from 5:1 to 1:5.

In an embodiment, ratio of transcutol P and Caprylocaproyl polyoxylglyceride is 1:1. In another embodiment as provided in batch 4, ratio of transcutol P and Caprylocaproyl polyoxylglyceride is 3:2. In yet another embodiment exemplified as example 2 and batches 7, 8, 9, 10 and 11, ratio of transcutol P and Caprylocaproyl polyoxylglyceride is 2:1. In an embodiment in batch G with 2:1 ratio of transcutol p and Caprylocaproyl polyoxylglyceride at least 50% release at the end of 4 hrs and at least 80% release at the end of 12 hrs is achieved.

In yet another embodiment, in place of carbomer, another agent is used such as Lauroyl polyoxylglycerides (Gelucire 44/14). Carbomer is hydrophilic in nature whereas Lauroyl polyoxylglycerides is a lipidic agent. Gelucire 44/14 provided a more sustained/controlled action. When Gelucire 44/14 was used for higher dose, a highly sustained release pattern was noted whereas various carbomer grades provided different desired release patterns for both low and high doses of GHK-Cu peptide.

Further, following trials incorporated higher dose of GHK-Cu peptide (10-20 mg or higher) using various grades of carbomer.

1. Batches 1-6 with Carbopol Ultrez 10;
2. Batches 7 and 8 with Carbopol 971 NF;
3. Batches 9-11 with Carbopol 974P NF.

All new batches with higher dose of GHK-Cu had incorporated dual penetration enhancer containing 20-40% of the total composition of transcutol p (Diethylene glycol mono ethyl ether) and from 10-20% of the total composition of Caprylocaproyl polyoxylglyceride. The batches incorporated 2:1, 3:2 and 1.66:1 ratio of these permeation enhancers.

Batches 2, 7, 10 and 11 are taken for In Vitro studies using Dialysis membrane with 12-14 kd molecular weight cut off and phosphate buffer of pH 7.4. Batches 2 and 7 exhibited around 30-35% release in 24 hrs but provided substantial release over 72 hrs. Batch 10 provided around 55% release in 24 hrs but substantial release in 48 hrs. Batch 11 provided around 79% release in 24 hrs.

Batch 11 was an intermediate batch showing intermediate release over 24 hrs. Its release was slower than batches G and H and faster than batches 2, 7 and 10. Hence, this batch was chosen for further studies which involved Ex-vivo and In-vivo animal studies.

Ex-Vivo studies on living tissue with a minimum change of natural conditions were conducted. For this study, porcine ear skin was used. The skin was procured from a local supplier and was properly cleaned and stored in saline solution. The skin was properly cut into circular shape so as to fit over the diffusion cell and the release studies were carried out. Batch 11 was tested Ex-vivo. It showed 59% release over 24 hrs.

Finally Batch 11 was subjected to In vivo animal studies. Sprague Dawley rats weighing 200-250 grams were used for the study. The aim was to find out whether batch 11 provides sustained release and steady state concentration In vivo. Transdermal patch incorporating 2 g gel composition of batch 11 was applied on each of the animals in an area of 4×4 square cms. Blood samples are collected at time intervals of 0.5, 1, 2, 4, 6, 8, 10, 12 and 24 hrs and the content of GHK-Cu was estimated. Surprisingly, it was observed that the steady state was readily achieved in an hour. As desired, steady state concentration over period of 24 hrs was achieved. Further, in compartmental analysis of plasma data for transdermal patch of GHK-Cu, the Pharmacokinetic parameter obtained were comparable to the actual parameters obtained.

The patch was removed after 24 hrs and un-permeated drug content was measured. When the patch was applied, it had 20 mg of dose of GHK-Cu. After the study, almost 70-90% of GHK-Cu had been retained in the patch in tested animals. This also indicated that lower doses of GHK-Cu of 1-2 mg would also work successfully. On the other hand, the same dose of 20 mg can be tried for 72 hrs or higher for 1-3 times a week application.

The transdermal patches of the present invention with lower and higher doses of GHK-Cu incorporating a gel reservoir composition provided sustained action and at the same time achieved steady state concentration in an hour which lasted for at least 24 hrs. By varying various pharmaceutical non-actives and their concentrations, various release patterns can be achieved. Dual penetration enhancer is most preferred which helped in instantly achieving steady state concentration in an hour. The gel reservoir helped in sustained release to maintain steady state for 24 hrs.

Transdermal patches can be prepared in various sizes including 2×2, 4×4, 6×6, 8×8 and 10×10 square cm. to apply on human skin based on the dose and requirement. Dose from 1 mg to 20 mg is found suitable if sufficient sustained action and sufficient amount of penetration enhancers are employed. Without carbopol is found preferred polymer for both higher and lower doses although other polymers can also be employed. Gelucire 44/14 was another desired polymer that can be used in place of carbopol. Various grades of carbopol provided different In Vitro release pattern. An intermediate batch 11 with intermediate release pattern was tested successfully In Vivo. From the blood samples collected, plasma was separated and stored for analysis. In Viva estimation of GHK-Cu was done by estimating Cu content of plasma samples using Atomic absorption spectroscopy and further correlating the GHK-Cu levels. This method was developed inhouse.

Table 18 provides predicted Pharmacokinetic parameter obtained after compartmental analysis of plasma data for transdermal patch of GHK-Cu for the Batch 11. Cmax of 13.28 µg/ml (predicted) vs. 14.71 µg/ml (observed) are quite consistent and such concentrations lasted for 24 hrs.

EXAMPLES

Comparative examples 1 and 2 are for comparisons only.

TABLE 3

| Comparative example 1 | | | | |
|---|---|---|---|---|
| Sr. no | Ingredients | Batch A | Batch B | Batch C |
| 1 | HPMC K100 | 0.1 | 0.15 | 0.2 |
| 2 | Triethanolamine | 0.4 | 0.4 | 0.4 |
| 3 | Methyl paraben | 0.75 | 0.75 | 0.75 |
| 4 | Propylene glycol(% v/w) | 30% | 30% | 30% |
| 5 | Distilled water | 20 | 20 | 20 |

Process:
1. Phase1: HPMC K100 is added in 10 ml distilled water under stirring at 700 rpm for 1 hr.
2. Phase2: Methyl paraben is added into propylene glycol under stirring and heated in water bath not exceeding temperature 60° C.

3. Then phase2 is added to phase1 under stirring. After complete addition, the solution is stirred for 5-10 mins to obtain uniform mixing. The volume is then made up to 20 ml using distilled water.
4. At the end the alkaline pH and gel formation is obtained using triethanolamine.

Figure 2:
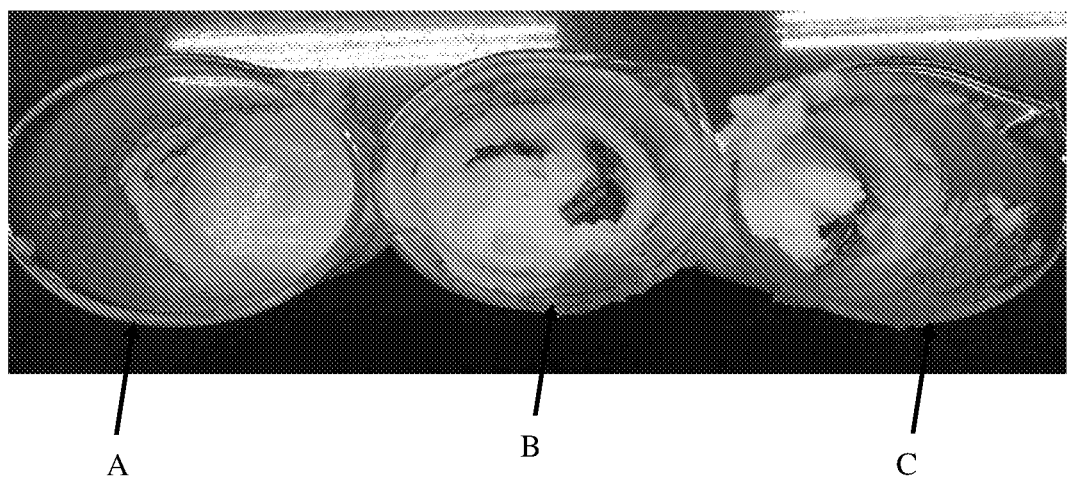
FIG. 2 provides image of transdermal gel prepared by using comparative example 1 batches A, B and C FIG. 3 provides image of transdermal gel prepared by using comparative example 2 batches D, E and F FIG. 4 provides image of transdermal gel prepared by using examples 2 and 3 i.e. batches G and H respectively.

Observation:

Gel did not form, when phase2 was added to phase1 it got precepted out. FIG. 2 provides image of transdermal gel prepared by using comparative example 1 batches A, B and C

TABLE 4

Comparative example 2

| Sr. no | Ingredients | Batch D | Batch E | Batch F |
|---|---|---|---|---|
| 1 | Carbopol 934 | 0.1 | 0.15 | 0.2 |
| 2 | Triethanolamine | 0.4 | 0.4 | 0.4 |
| 3 | Methyl paraben | 0.75 | 0.75 | 0.75 |
| 4 | Propylene glycol(% v/w) | 30% | 30% | 30% |
| 5 | Distilled water | 20 | 20 | 20 |

Process
1. Phase1: Carbolpol 940 is added in 10 ml distilled water under stirring at 700 rpm for 1 hr.
2. Phase2: Methyl paraben is added into propylene glycol under stirring and heated in water bath not exceeding temperature 60° C.
3. Then phase2 is added to phase1 under stirring. After complete addition, the solution is stirred for 5-10 mins to obtain uniform mixing. The volume is then made up to 20 ml using distilled water.
4. At the end the alkaline pH and gel formation is obtained using triethanolamine.

Observation

Figure 3:
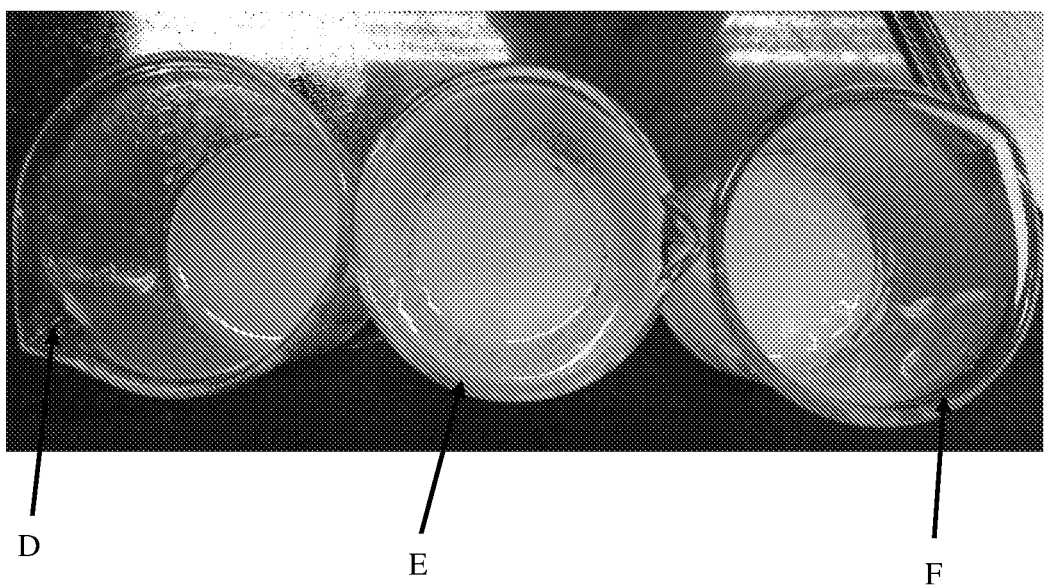

White coloured gels are formed having pH 6.4, 6.3 and 6.9 for batch7, 8 and 9. FIG. 3 provides image of transdermal gel prepared by using comparative example 2 batches D, E and F.

Following examples do not limit the scope of the invention.

Example 1

TABLE 5

Formulation with Carbopol or polyoxylglycerides/Polyoxyl stearate

| Ingredients | Quantity % | Quantity % |
|---|---|---|
| GHK-cu | 0.05-20 | 0.05-20 |
| Carbopol | Up to 4% | — |
| Lauroyl polyoxylglycerides/Stearoyl polyoxylglycerides/Polyoxyl stearate | — | Up to 80% |
| Caprylocaproyl polyoxylglycerides (Labrasol) | 0-20 | 0-20 |
| Diethylene glycol monoethyl ether (Transcutol P) | 0.5-20 | 0.5-20 |
| triethanolamine | q.s. to adjust pH to 7.4 | — |
| Distilled water | q.s | — |
| Acrylic Adhesive | 10-50 | 10-50 |
| Silicone Adhesive | 10-50 | 10-50 |

Process for carbopol based gel
1. Preformed GHK-Cu complex is dissolved in distilled water to form drug phase.
2. Carbopol 934 is added in drug phase under stirring. Once carbopol 934 is completely dissolved, it is further stirred for 1 hr.
3. Transcutol P and; Labrasol if needed are added to above solution.
4. The pH is adjusted to 7.4 using triethanolamine to form gel.
5. Quantity is adjusted with water to form desired quantity of gel.
6. The above formulation will be incorporated in the transdermal patch.

Following examples do not limit the scope of the invention. They provide manufacturing of low and high doses of GHK-Cu, In vitro release of manufactured batches of GHK-Cu, Ex-Vivo studies on Batch 11 of GHK-Cu and In vivo study on Batch 11 of GHK-Cu.

Batches with lower amounts of GHK-Cu wherein dose is 1 mg.

Example 2

TABLE 6

Formulation with Carbopol - Batch G

| Ingredients | Quantity % |
|---|---|
| GHK-cu | 0.05 |
| Carbopol 934 | 1% |
| Caprylocaproyl polyoxylglycerides (Labrasol) | 2.5 |
| Diethylene glycol monoethyl ether (Transcutol P) | 5.0 |
| triethanolamine | q.s. to adjust pH to 7.4 |
| Distilled water | q.s. to 100 |

Process
1. Preformed GHK-Cu complex is dissolved in distilled water to form drug phase.
2. Carbolpol 934 is added in drug phase under stirring. Once carbolpol 934 is completely dissolved it is stirred for 1 hr.
3. Transcutol P and Labrasol are added to above solution.
4. The pH is adjusted to 7.4 using triethanolamine to form gel.
5. Quantity is adjusted with water to form desired quantity of gel.

Figure 4:
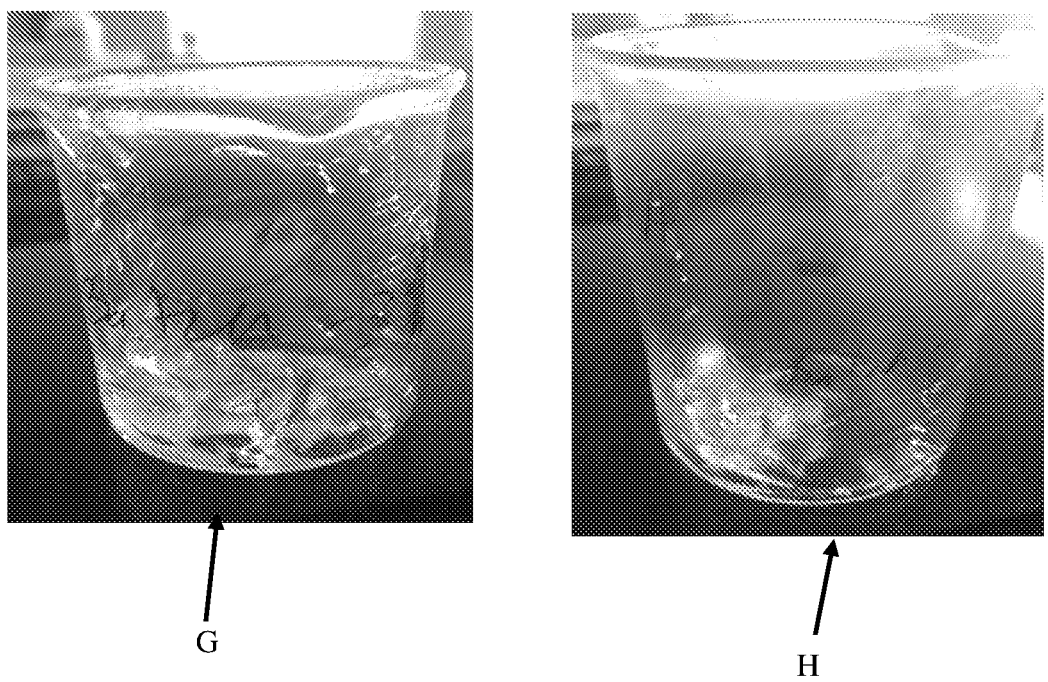

FIG. 4 provides image of transdermal gel prepared by using example 2 batch G.

Example 3

TABLE 7

Formulation with Carbopol - Batch H

| Ingredients | Quantity % |
|---|---|
| GHK-cu | 0.05 |
| Carbopol 934 | 1 |
| Caprylocaproyl polyoxylglycerides (Labrasol) | 0 |
| Diethylene glycol monoethyl ether (Transcutol P) | 5 |
| triethanolamine | q.s. to adjust pH to 7.4 |
| Distilled water | q.s. to 100 ml |

Process
1. Preformed GHK-Cu complex is dissolved in distilled water to form drug phase.
2. Carbolpol 934 is added in drug phase under stirring. Once carbolpol 934 is completely dissolved it is stirred for 1 hr.
3. Transcutol P is added to above solution.

4. The pH is adjusted to 7.4 using triethanolamine to form gel.
5. Quantity is adjusted with water to form desired quantity of gel.

FIG. 4 provides image of transdermal gel prepared by using example 3 batch H.

Example 4

TABLE 8

Formulation with copolymer of ethylene and vinyl acetate

| Ingredients | Quantity % |
|---|---|
| GHK-cu | 0.05-20 |
| copolymer of ethylene and vinyl acetate | 50-96 |
| Isopropyl myristate | 5-10 |
| Caprylocaproyl polyoxylglycerides (Labrasol) | 0-20 |
| Diethylene glycol monoethyl ether (Transcutol P) | 0.5-20 |
| Glyceryl monolaureate | 2-8 |
| Acrylic Adhesive | 10-50 |
| Silicone Adhesive | 10-50 |

Example 5

TABLE 9

Formulation with Poly(Butyl methacrylate, methyl methacrylate)

| Ingredients | Quantity % |
|---|---|
| GHK-cu | 0.05-20 |
| Poly(Butyl methacrylate, methyl methacrylate) | 20-80 |
| Isopropyl myristate | 5-10 |
| Glyceryl monolaureate | 2-8 |
| Caprylocaproyl polyoxylglycerides (Labrasol) | 0-20 |
| Diethylene glycol monoethyl ether (Transcutol P) | 0.5-20 |
| Acrylic Adhesive | 10-50 |
| Silicone Adhesive | 10-50 |

Process
1. Poly(Butyl methacrylate, methyl methacrylate) is dissolved in a suitable solvent followed by addition of GHK-cu and addition of other excipients.
2. The above dispersion/solution is mixed until uniform homogenous solution/dispersion is obtained.
3. The volatile solvent from above dispersion/solution is evaporated using suitable method
4. The above formulation will be incorporated in the transdermal patch

Example 6: In-vitro Release of Example 2

TABLE 10

In vitro release of batch G of example 2

| Sr. No. | Time in hrs | % In vitro Release |
|---|---|---|
| 1 | 2 | 44.41 |
| 2 | 4 | 57.97 |
| 3 | 8 | 77.40 |
| 4 | 12 | 96.95 |
| 5 | 24 | 102.77 |

Figure 5:
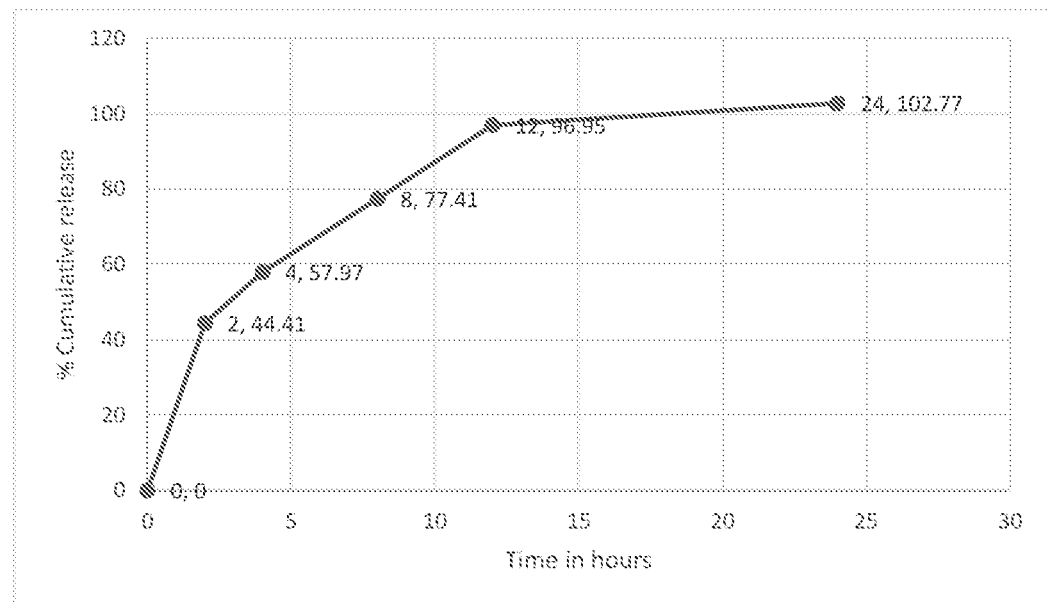
FIG. 5 provides In-vitro release of transdermal gel prepared according to the present invention as provided in example 2-batch G.

FIG. 5 provides In-vitro release of transdermal gel prepared according to the present invention as provided in example 2-batch G.

Example 7: In-vitro Release of Example 3

TABLE 11

In vitro release of batch H of example 3

| Sr. No. | Time in hrs | % In vitro Release |
|---|---|---|
| 1 | 2 | 33.69% |
| 2 | 4 | 48.76% |
| 3 | 8 | 71.44 |
| 4 | 12 | 93.47 |
| 5 | 24 | 97.52 |

Figure 6:
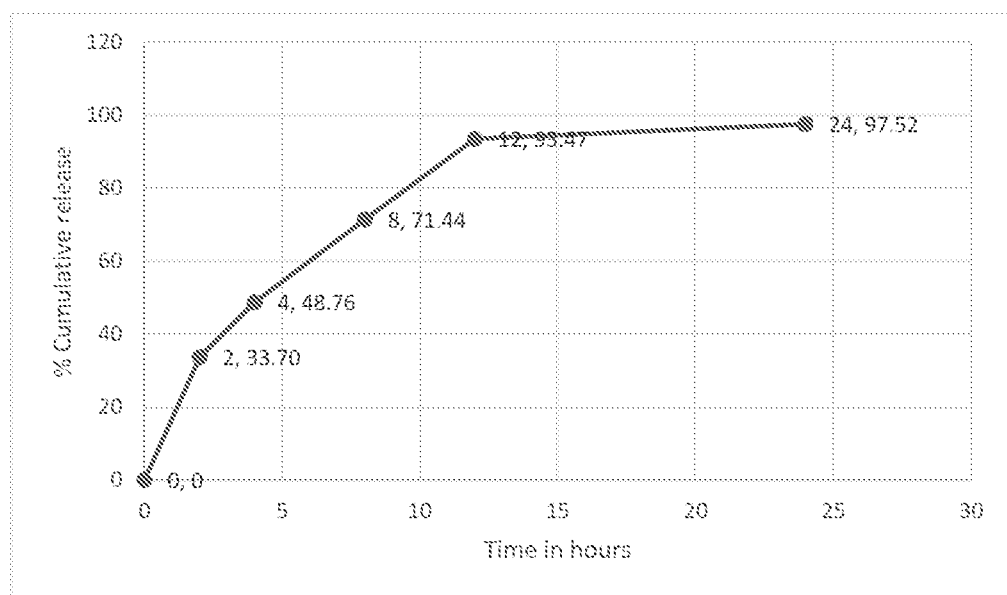
FIG. 6 provides In-vitro release of a transdermal patch according to the present invention as provided in example 3-batch H.

FIG. 6 provides In-vitro release of a transdermal patch according to the present invention as provided in example 3-batch H.

Batches with higher amounts of GHK-Cu wherein dose is 20 mg.

Example 8

TABLE NO 12

Formulation of batches using Carbopol Ultrez 10

| Ingredients | Batch 1 | Batch 2 | Batch 3 | Batch 4 | Batch 5 | Batch 6 |
|---|---|---|---|---|---|---|
| | % w/w | | | | | |
| GHK-Cu | 1 | 1 | 1 | 1 | 1 | 1 |
| Carbopol Ultrez 10 | 2 | 1 | 1 | 2 | 1 | 1 |
| Diethylene glycol mono ethyl ether | 20 | 20 | 25 | 30 | 30 | 40 |
| Caprylocaproyl polyoxyl-8 glycerides | 10 | 10 | 15 | 20 | 20 | 20 |
| Triethanolamine (10%) | 8 | 8 | 8 | 8 | 8 | 8 |
| Distilled water | qs | qs | qs | qs | qs | qs |

TABLE NO 13

Formulation of batches using Carbopol 971P NF

| Ingredients | Batch 7 | Batch 8 |
|---|---|---|
| | % w/w | |
| GHK-Cu | 1 | 1 |
| Carbopol 971 NF | 4 | 4 |
| Caprylocaproyl polyoxyl-8 glycerides | 10 | 20 |
| Diethylene glycol mono ethyl ether | 20 | 40 |
| Triethanolamine (10%) | 8' | 8 |
| Distilled water | q.s. | q.s. |

TABLE NO 14

Formulation of batches using Carbopol 974P NF

| Ingredients | Batch 9 | Batch 10 | Batch 11 |
|---|---|---|---|
| | % w/w | | |
| GHK-Cu | 1 | 1 | 1 |
| Carbopol 974P NF | 1 | 1.5 | 1.5 |
| Caprylocaproyl polyoxyl-8 glycerides | 10 | 10 | 20 |

TABLE NO 14-continued

Formulation of batches using Carbopol 974P NF

| Ingredients | Batch 9 | Batch 10 % w/w | Batch 11 |
|---|---|---|---|
| Diethylene glycol mono ethyl ether | 20 | 20 | 40 |
| Triethanolamine | 8 | 8 | 8 |
| Distilled water | qs | qs | qs |

Process of preparation of batches 1-11 is same as that described under example 2 for batch G.

Example 9

Physicochemical Evaluation of the Gel

Description: 1 gram of the sample was taken in a petri plate and examined visually for its appearance.

Standard Plot: Solutions of different concentration of GHK-Cu viz. 20 ppm, 40 ppm, 60 ppm, 80 ppm, 100 ppm were prepared in phosphate buffer pH 7.4 and the absorbance was measured at 227 nm. This standard plot was used for diffusion studies.

Also a separate standard plot was prepared in water for same concentration of 20 ppm, 40 ppm, 60 ppm, 80 ppm, 100 ppm. and the prepared standard plot was used for the calculation of drug content in the gel formulation.

Example 10

Procedure for Determination of Drug Content:
1. Gel equivalent to 0.5 mg of drug was weighed and dissolved in 5 ml distilled water.
2. 1 ml of solution was transferred to another volumetric flask and volume was made upto 10 ml.
3. Again 1 ml of above solution was transferred to another volumetric flask and volume was made upto 10 ml.
4. Absorbance was measured at 227 nm and drug content was calculated.

Example 11

In vitro Drug Release Study:

For the in vitro drug release testing, selection of an appropriate receiving medium and that of the membrane is extremely important.

Selection of the Membrane:

The membrane should be able to provide an inert surface for holding the drug formulation. Most importantly, it should allow the free passage of the drug without causing any hindrance to the diffusion. Also, a hydrophilic membrane is selected for a hydrophobic moiety and vice versa.

Selection of Diffusion Medium: The receiving medium placed in the diffusion cells must be one which mimics the physiological condition of the skin. It must be able to solubilize the active ingredient and provide as a sink for the drug. pH of the medium should also be carefully selected to cater to the need as per the pH of the drug formulation, pH solubility profile of the active and also pH of the target membrane. pH of Media was selected as Phosphate Buffer pH 7.4.

Temperature: In most cases where the dosage form is applied to skin, 32° C. is appropriate. Exceptions are when the target organ is a membrane such as vaginal mucosa, in which case, 37° C. is more appropriate. We used 37° C. in all the experiments.

Sampling Intervals: 2 hr, 4 hr, 6 hr, 8 hr, 10 hr, 12 hr and 24 hr.

Sampling Volume: 1 ml at each time point is withdrawn and replaced with fresh medium.

Membrane: Dialysis membrane with 12-14 kd molecular weight cut off.

Table 15 provides In-vitro release study of batches 2, 7, 10 and 11. The corresponding graph is presented in FIG. 7.

TABLE NO 15

GHK-Cu Release data

| | % Drug Released | | | |
|---|---|---|---|---|
| Time in hrs | Batch 2 | Batch 7 | Batch 10 | Batch 11 |
| 1 | 11.355 | | | 20.364 |
| 2 | | 12.73 | 8.171 | |
| 3 | 15.819 | | | |
| 4 | | 14.46 | 14.238 | 30.541 |
| 6 | 18.494 | 16.31 | 22.089 | 35.045 |
| 8 | | 17.85 | 31.563 | 40.796 |
| 9 | 25.772 | | | |
| 10 | | 19.67 | 43.87 | 51.45 |
| 12 | 31.031 | 21.58 | | |
| 24 | 32.433 | 30.11 | 55.404 | 79.168 |

Example 12

Ex-Vivo Studies:

Batch 11 was finalised for ex-vivo studies and the release were carried out on Porcine ear skin. The % drug release at 24 h was found out to be 59%. The % release has reduced to 59% in ex-vivo from 79% in-vitro. This was attributed to the thickness of the porcine ear skin.

Figure 8:
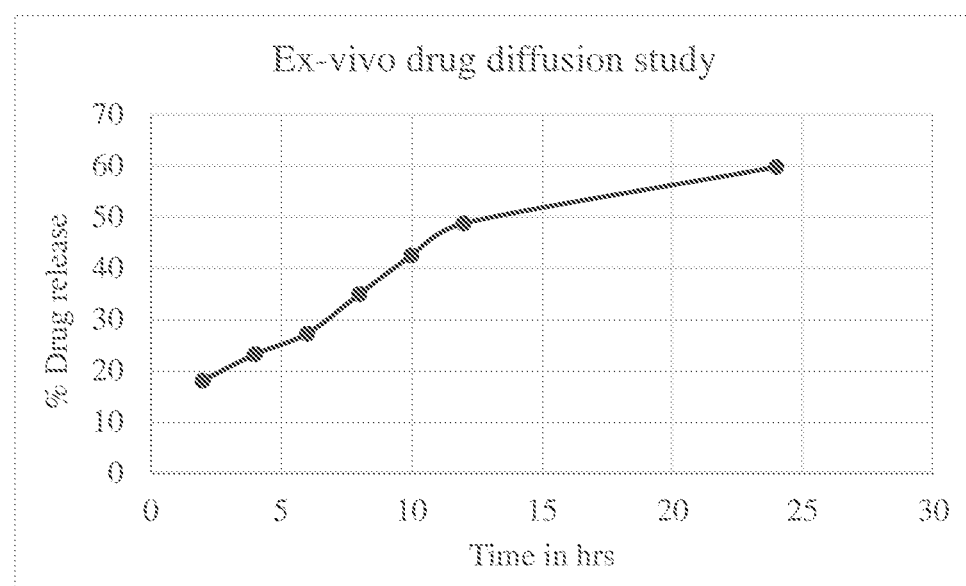
FIG. 8 provides Ex-vivo (diffusion) release using porcine ear skin of a transdermal patch incorporating batch 11.

Table 16 and FIG. 8 provide Ex-vivo results of batch 11.

TABLE NO 16

Release data across Porcine Skin

| Time | % Drug Released |
|---|---|
| 2 | 18.02 |
| 4 | 23.16 |
| 6 | 27.19 |
| 8 | 34.9 |
| 10 | 42.44 |
| 12 | 48.71 |
| 24 | 59.73 |

Example 13

In-Vivo Studies:

Batch 11 was chosen for in-vivo pharmacokinetic study using Sprague Dawley rats. The study included application of transdermal patch having a size of 4×4 cm$^2$. Since rats inherently have GHK-Cu, initial level of GHK-Cu before application of patch is estimated to find out the difference in the GHK-Cu levels before and after application. Each patch has 1 GHK-Cu in 2 g gel reservoir. The patch is applied on 12 rats. Thus, each rat is dosed with 1% of 2 g i.e. 20 mg of GHK-Cu. After administration of patch, blood samples are collected as per the designed protocol. The time intervals for the study were as follows: 0.5 hr, 1 hr, 2 hr, 4 hr, 6 hr, 8 hr, 10 hr, 12 hr, 24 hr after application of a patch. The blood samples were collected at designed time intervals and the plasma was obtained from each sample by separation with the help of centrifugation. The plasma obtained was analysed for the presence of Copper using Atomic Absorption Spectroscopy.

Experimental Design:
  Application: Formulation patches were applied on the skin of the rats after proper hair removal process.
  Collection of Blood Samples: Blood samples were collected at 0.5, 1, 2, 4, 6, 8, 10, 12, 24 hours through retro orbital plexus using a glass capillary after anesthesia.
  Dosing: The gel patch formulation was applied on the animal skin only once at the start of the study.
  Method: Sprague Dawley rats weighing 200-250 grams were used for the study. Animals were kept in laboratory for 3-4 days for acclimatization, with free access to food and water.
  Substance: GHK-Cu in a transdermal gel patch
  Dose: 20 mg of GHK-Cu per patch per animal
  Sites: Skin
  Volume: Volume of blood withdrawal: 1-1.5 ml.
  Volume of total blood in rat weighing 250 g: 20-22

Animals Required:
  a. Species/Common name—Sprague Dawley rats
  b. Age weight/size—200-250 grams
  c. Gender—Male/Female (any)
  d. Number to be used—12
  e. Number of days each animal to be housed—1 months Result of Atomic Absorption Spectroscopy (AAS) Study As per the study design, blood samples were collected from the study animals at predetermined time interval. Plasma was separated from the freshly collected blood samples and stored for analysis.

Atomic absorption spectroscopy was utilized to measure the Cu concentration in the collected plasma sample using a validated Cu estimation methodology developed by the analytical lab. The Cu content measured was correlated with the GHK-Cu concentration by theoretical calculation and levels have been reported in the table no. 11 shown below.

Figure 9:
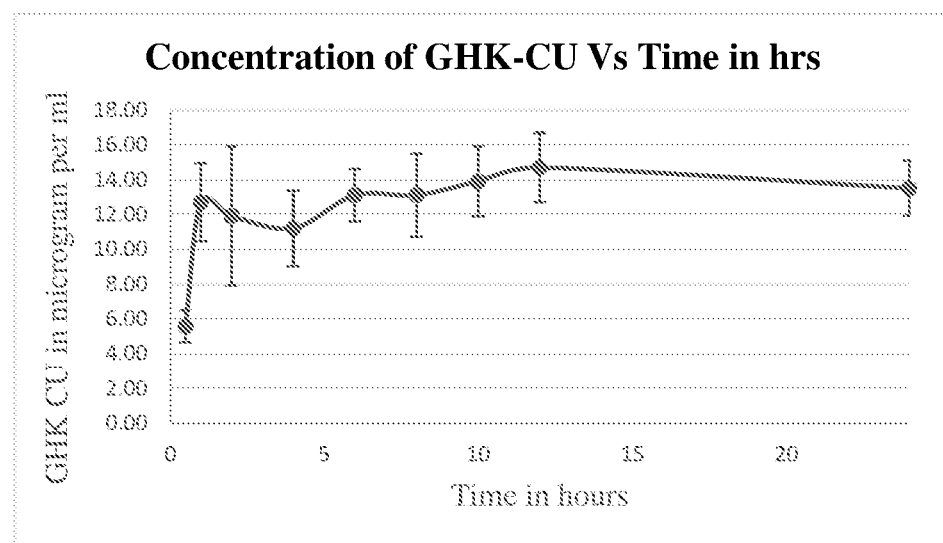
FIG. 9 provides plot of In vivo concentration of GHK-Cu vs. time in hrs.

Table 17 and FIG. 9 provide plasma concentration Vs time profile for the Batch 11.

TABLE NO 17

Avg. Conc. of GHK Cu (µg/ml) observed in rat plasma for 24 hrs

| Time in hr | Avg. conc. of Cu (µg/ml) | SD | Avg. Conc. GHK Cu (µg/ml) | SD |
| --- | --- | --- | --- | --- |
| 0 | 0.725 | 0.35 | 4.61 | 2.23 |
| 0.5 | 0.88 | 0.14 | 5.57 | 0.89 |
| 1 | 2.00 | 0.35 | 12.72 | 2.23 |
| 2 | 1.88 | 0.63 | 11.93 | 4.01 |
| 4 | 1.76 | 0.34 | 11.21 | 2.16 |
| 6 | 2.06 | 0.24 | 13.12 | 1.53 |
| 8 | 2.06 | 0.38 | 13.12 | 2.42 |
| 10 | 2.19 | 0.31 | 13.91 | 1.97 |
| 12 | 2.31 | 0.31 | 14.71 | 1.97 |
| 24 | 2.13 | 0.25 | 13.52 | 1.59 |

Figure 10:
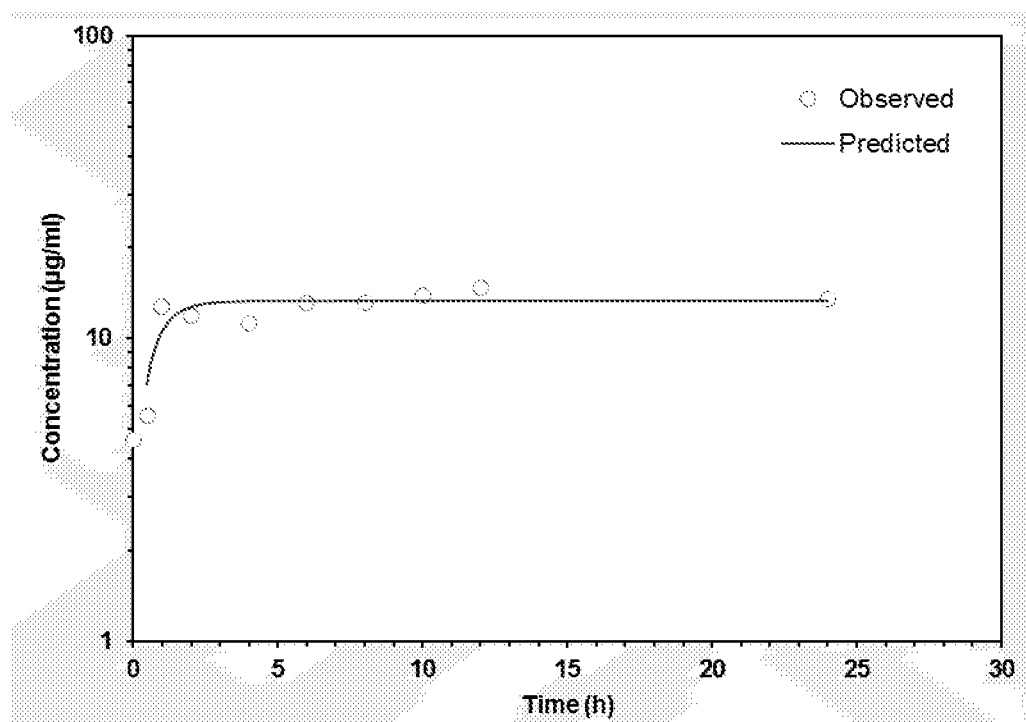
FIG. 10 provides log concentration of GHK-Cu vs. time of predicted and observed data.

Table 18 provides predicted Pharmacokinetic parameter obtained after compartmental analysis of plasma data for transdermal patch of GHK-Cu for the Batch 11. FIG. 10 provides predicted and observed profile of log concentration of GHK-Cu vs time in hrs.

TABLE NO 18

Pharmacokinetic parameter for transdermal patch of GHK-Cu.

| Parameter | Unit | Value |
| --- | --- | --- |
| Tmax | h | 9.101 |
| Cmax | µg/ml | 13.287 |
| AUC 0-t | µg/ml*h | 310.418 |

We claim:

1. A transdermal delivery composition of GHK-Cu peptide (copper tripeptide) for avoiding first pass metabolism comprising:
  a topically applied composition comprising GHK-Cu peptide or copper tripeptide, a polymer and one or more penetration enhancers, the composition transdermally delivering GHK-Cu peptide or copper tripeptide while avoiding first pass metabolism.

2. The composition of GHK-Cu peptide of claim 1, wherein the topically applied composition is a transdermal composition comprising from 0.5 mg to 200 mg of GHK-Cu peptide or copper tripeptide.

3. The composition of GHK-Cu peptide of claim 2, wherein the transdermal composition sustains constant plasma levels of GHK-Cu peptide or copper tripeptide in an animal for at least 12 hours after application.

4. The composition of GHK-Cu peptide of claim 2, wherein the transdermal composition sustains constant plasma levels of GHK-Cu peptide or copper tripeptide in an animal for at least 24 hours after application.

5. The composition of GHK-Cu peptide of claim 2, wherein the transdermal composition sustains constant plasma levels of GHK-Cu peptide or copper tripeptide in an animal from at least 48 hours to 72 hours after application.

6. The composition of GHK-Cu peptide of claim 2, wherein the transdermal composition sustains in an animal at least 50% of plasma levels of GHK-Cu peptide or copper tripeptide of maximum plasma concentration for at least 12 hours.

7. The composition of GHK-Cu peptide of claim 2, wherein the transdermal composition sustains in an animal at least 50% of plasma levels of GHK-Cu peptide or copper tripeptide of maximum plasma concentration for at least 24 hours.

8. The composition of GHK-Cu peptide of claim 6, wherein the transdermal composition sustains in an animal at least 70% of plasma levels of GHK-Cu peptide or copper tripeptide of maximum plasma concentration for at least 12 hours.

9. The composition of GHK-Cu peptide of claim 7, wherein the transdermal composition sustains in an animal at least 70% of plasma levels of GHK-Cu peptide or copper tripeptide of maximum plasma concentration for at least 24 hours.

10. The composition of GHK-Cu peptide of claim 2, wherein the transdermal composition provides at least one of the following release patterns in an In Vitro study employing dialysis membrane and a phosphate buffer of pH 7.4:
  i) at least 30% release in 24 hours and 70% release in 72 hours;
  ii) at least 50% release in 24 hours;
  iii) at least 70% release in 24 hours;
  iv) at least 80% release in 24 hours; and
  v) at least 90% release in 24 hours.

11. The composition of GHK-Cu peptide of claim 2, wherein the polymer includes a member selected from the group consisting of polyethylene glycol, methacrylate copolymers, acrylic copolymer, polyester film/copolymer of ethylene and vinyl acetate, poly(butyl methacrylate-co-methyl methacrylate), carboxymethylcellulose, ethyl cellulose, hydroxypropylmethylcellulose, hydroxypropylcellulose, polyvinylpyrrolidone, and polymer of acrylic acid cross-linked with allyl ethers of polyalcohols.

12. The composition of GHK-Cu peptide of claim 2, wherein the penetration enhancer includes a member selected from the group consisting of dimethyl sulfoxide (DMSO), dimethyl formamide, ethanol, propylene glycol, octyl alcohol, caprylocaproyl polyoxyl-8 glycerides and diethylene glycol monoethyl ether, ethyl oleate, isopropyl myristate, glyceryl monolaureate, and silicone oil.

13. The composition of GHK-Cu peptide of claim 2, wherein the transdermal composition includes from 0.5 to 10% of the polymer, and from 5 to 80% of the penetration enhancers.

14. The composition of GHK-Cu peptide of claim 13, wherein the transdermal composition includes from 0.5 to 5% of the polymer, and from 5 to 60% of the penetration enhancers.

15. The composition of GHK-Cu peptide of claim 1, wherein the polymer is a polymer of acrylic acid crosslinked with allyl ethers of polyalcohols.

16. The composition of GHK-Cu peptide of claim 1, wherein the penetration enhancer includes a member selected from the group consisting of caprylocaproyl polyoxyl-8 glycerides, diethylene glycol monoethyl ether, and Isopropyl myristate.

* * * * *